(12) United States Patent
Shibuya et al.

(10) Patent No.: US 8,939,896 B2
(45) Date of Patent: Jan. 27, 2015

(54) ATTACHMENT FOR ENDOSCOPE AND ENDOSCOPE SYSTEM

(75) Inventors: Hiroshi Shibuya, Kanagawa (JP); Nobuyuki Torisawa, Kanagawa (JP); Koji Yoshida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 87 days.

(21) Appl. No.: 13/286,846

(22) Filed: Nov. 1, 2011

(65) Prior Publication Data

US 2012/0116167 A1    May 10, 2012

(30) Foreign Application Priority Data

Nov. 4, 2010    (JP) .................................. 2010-247662

(51) Int. Cl.
*A61B 1/04*    (2006.01)
*A61B 1/015*    (2006.01)
*A61B 1/00*    (2006.01)

(52) U.S. Cl.
CPC ......... *A61B 1/00089* (2013.01); *A61B 1/00091* (2013.01); *A61B 1/015* (2013.01)
USPC .......................................... 600/127; 600/129

(58) Field of Classification Search
USPC ........................... 600/127, 128, 129, 156–159
See application file for complete search history.

(56) References Cited

U.S. PATENT DOCUMENTS

| | | | |
|---|---|---|---|
| 3,903,877 A | 9/1975 | Terada | |
| 5,855,549 A | 1/1999 | Newman | |
| 6,916,284 B2 * | 7/2005 | Moriyama | 600/127 |
| 2004/0260149 A1 * | 12/2004 | Ishibiki | 600/127 |
| 2007/0066870 A1 * | 3/2007 | Ohashi et al. | 600/127 |
| 2007/0163585 A1 | 7/2007 | Uesugi et al. | |
| 2007/0255165 A1 | 11/2007 | Uesugi et al. | |
| 2009/0198212 A1 * | 8/2009 | Timberlake et al. | 604/506 |
| 2010/0010301 A1 * | 1/2010 | Hale et al. | 600/109 |
| 2012/0071724 A1 * | 3/2012 | Hashido et al. | 600/175 |

FOREIGN PATENT DOCUMENTS

| | | | |
|---|---|---|---|
| DE | 30 04 089 A1 | 8/1980 | |
| JP | 01229220 A  * | 9/1989 | ............ G02B 23/24 |
| JP | 7-313443 A | 12/1995 | |

(Continued)

OTHER PUBLICATIONS

Notification of Reason(s) for Rejection dated Oct. 25, 2012, with English translation.

(Continued)

*Primary Examiner* — Alireza Nia
*Assistant Examiner* — Timothy J Neal
(74) *Attorney, Agent, or Firm* — McGinn IP Law Group, PLLC

(57) ABSTRACT

Provided is an attachment for an endoscope, the attachment being attached to a leading end part of the endoscope having a leading end surface on which an observation window for observing an inside of a subject's body and a first opening for jetting a constant-pressure supplied gas are formed, the attachment including: a second opening provided at a position separate from the leading end surface; a pipe conduit that communicates the first opening and the second opening with each other so as to jet the constant-pressure supplied gas from the second opening; and a region separating member that separates a jetting region of the constant-pressure supplied gas jetted from the second opening from a region of view of the observation window.

11 Claims, 7 Drawing Sheets

(56) References Cited

FOREIGN PATENT DOCUMENTS

| JP | 2002-233491 A | 8/2002 |
| JP | 2005-80866 A | 3/2005 |
| JP | 2005-253873 A | 9/2005 |
| JP | 2006-325816 A | 12/2006 |
| JP | 2009-106360 A | 5/2009 |
| WO | WO 2007/080971 A1 | 7/2007 |

OTHER PUBLICATIONS

European Search Report dated Feb. 3, 2012.
Notification of Reason(s) for Rejection dated May 31, 2013, with English translation.
Chinese Office Action dated Aug. 29, 2014 with English Translation.

* cited by examiner

ATTACHMENT FOR ENDOSCOPE AND ENDOSCOPE SYSTEM

BACKGROUND OF THE INVENTION

1. Field of the Invention

The present invention relates to an attachment for an endoscope and an endoscope system, and more particularly, to an attachment for an endoscope and an endoscope system that are used for an endoscope in which a constant-pressure gas is supplied from a gas supply apparatus into a lumen of a subject via an opening provided in a leading end part of a flexible endoscope inserted into the lumen, to thereby perform observation and treatment of the inside of the lumen.

2. Description of the Related Art

Up to now, in medical fields, a medical diagnosis utilizing an endoscope is widely performed. In particular, an image-pickup element such as a CCD is built in an insertion leading end part of the endoscope inserted into a body cavity, and an image inside of the body cavity is photographed by the built-in image-pickup element. The image is subjected to signal processing by a processor apparatus to be displayed on a monitor. A doctor observes for a diagnosis the processed image. Otherwise, a treatment tool is inserted from a channel for treatment tool insertion, to thereby perform treatment, for example, collection of a sample and excision of a polyp.

In particular, a flexible insertion part of a flexible endoscope is inserted into a lumen of a stomach, a large intestine, or other organs, and diagnosis and treatment are performed on the inside of the lumen. In this case, a treatment tool is inserted into the lumen via a forceps channel (treatment tool channel) of the flexible endoscope, to thereby perform the curative treatment.

At this time, in order to secure the field of view of the flexible endoscope and secure space for operating the treatment tool, a constant-pressure supplied gas such as carbon dioxide gas is supplied into the lumen for the purpose of inflating the lumen.

For example, Japanese Patent Application Laid-Open No. 2009-106360 discloses a laparoscope-assisted surgery system including two endoscopes, that is, a rigid endoscope and a flexible endoscope, in which: a plurality of trocars are inserted into an abdomen of a patient; the rigid endoscope is inserted into an abdominal cavity from one of the trocars; an insufflation gas supplied from an insufflation apparatus is guided into the abdominal cavity via the other trocars; and the flexible endoscope is further inserted into a lumen of a large intestine or other organs. Then, in this system, carbon dioxide gas, which is adjusted to a predetermined pressure, is guided into the abdominal cavity via the other trocars and carbon dioxide gas is also supplied into the lumen via a treatment tool channel of the flexible endoscope, as the insufflation gas from the insufflation apparatus.

Unfortunately, in the case as in the above-mentioned conventional example where a constant-pressure gas is supplied via an opening of the treatment tool channel, such as a forceps port, formed in a leading end part of the flexible endoscope, bubbles are generated near a gas jetting port by a bodily fluid or water attached to a leading end surface of the endoscope, and the bubbles are attached to an observation window (image-pickup apparatus) formed on the leading end surface, so that the field of view is blocked unfavorably.

SUMMARY OF THE INVENTION

The present invention has been made in view of the above-mentioned circumstances, and therefore has an object to provide an attachment for an endoscope and an endoscope system that can prevent bubbles generated near a gas jetting port from blocking the field of view of an observation window when a constant-pressure gas is supplied via an opening formed on a leading end surface of a flexible endoscope, to thereby secure the field of view.

In order to achieve the above-mentioned object, a first aspect of the present invention provides an attachment for an endoscope, the attachment being attached to a leading end part of the endoscope having a leading end surface on which an observation window for observing an inside of a subject's body and a first opening for jetting a constant-pressure supplied gas are formed, the attachment including: a second opening provided at a position separate from the leading end surface; a pipe conduit that communicates the first opening and the second opening with each other so as to jet the constant-pressure supplied gas from the second opening; and a region separating member that separates a jetting region of the constant-pressure supplied gas jetted from the second opening from a region of view of the observation window.

With this configuration, a jetting port of the constant-pressure supplied gas is separated from the leading end surface on which the observation window is formed, and the jetting region of the constant-pressure supplied gas is separated by the region separating member from the region of view of the observation window. Accordingly, even if bubbles are generated by the constant-pressure supplied gas jetted near the jetting port of the constant-pressure supplied gas, the bubbles are prevented from moving toward the region of view of the observation window, so that the field of view of the observation window can be secured.

In addition, according to a second aspect of the present invention, the region separating member is a hood fitted onto an outer circumferential surface of the leading end part.

With this configuration, the jetting region of the constant-pressure supplied gas can be easily separated from the region of view of the observation window.

In addition, according to a third aspect of the present invention, the second opening is formed on a side surface of the hood on a side close to the first opening.

With this configuration, because the constant-pressure supplied gas can be jetted to the outside of the hood, the bubbles generated near the jetting port can be prevented from moving toward the observation window.

In addition, according to a fourth aspect of the present invention, the pipe conduit is a pipe-like member that is bent in an L-shape and includes: a horizontal part perpendicular to an axial direction of the endoscope; and a vertical part parallel to the axial direction of the endoscope, with the pipe-like member being attached to the leading end part of the endoscope, and the pipe conduit is provided to the hood so that the horizontal part is coupled to the second opening and the vertical part can be coupled to the first opening.

With this configuration, because the constant-pressure supplied gas can be jetted to the outside of the hood via the pipe conduit, the generated bubbles can be prevented from blocking the field of view of the observation window.

In addition, according to a fifth aspect of the present invention, the attachment for an endoscope further includes an O-ring that is provided in a leading end part of the vertical part of the pipe conduit, the leading end part being coupled to the first opening.

With this configuration, airtightness at a coupling portion between the first opening and the pipe conduit can be secured.

In addition, according to a sixth aspect of the present invention, the region separating member is a wall-like member that is formed so as to follow an outer circumferential surface of the leading end surface on a side on which the first opening is formed.

As described above, only part of the outer circumference of the leading end part is surrounded by the wall-like member instead of the hood that surrounds the entire outer circumference thereof. Also with this configuration, the jetting region of the constant-pressure supplied gas can be easily separated from the region of view of the observation window.

In addition, according to a seventh aspect of the present invention, the wall-like member has a shape obtained by obliquely cutting out a leading end of a cylinder.

With this configuration, the region separating member can be easily made, and a shape without a corner portion does not damage the inside of the subject's body.

In addition, according to an eighth aspect of the present invention, the second opening is formed in the wall-like member.

With this configuration, because the constant-pressure supplied gas can be jetted to the outside of the wall-like member, the bubbles generated near the jetting port can be prevented from moving toward the observation window.

In addition, according to a ninth aspect of the present invention, the pipe conduit is a pipe-like member that is bent in an L-shape and includes: a horizontal part perpendicular to an axial direction of the endoscope; and a vertical part parallel to the axial direction of the endoscope, with the pipe-like member being attached to the leading end part of the endoscope, and the pipe conduit is provided to the wall-like member so that the horizontal part is coupled to the second opening and the vertical part can be coupled to the first opening.

With this configuration, because the constant-pressure supplied gas can be jetted to the outside of the wall-like member via the pipe conduit, the generated bubbles can be prevented from blocking the field of view of the observation window.

In addition, according to a tenth aspect of the present invention, the attachment for an endoscope further includes an O-ring that is provided in a leading end part of the vertical part of the pipe conduit, the leading end part being coupled to the first opening.

With this configuration, airtightness at a coupling portion between the first opening and the pipe conduit can be secured.

In addition, according to an eleventh aspect of the present invention, an entire body of the pipe conduit is provided in a region outside of view that is outside of the region of view of the observation window.

With this configuration, the pipe conduit that is provided for jetting the constant-pressure supplied gas to the outside of the region of view of the observation window does not block the field of view of the observation window.

Similarly, in order to achieve the above-mentioned object, a twelfth aspect of the present invention provides an endoscope system including the attachment for an endoscope according to any one of the first to eleventh aspects.

With this configuration, in the case where the constant-pressure supplied gas is supplied from the leading end surface of the leading end part of the endoscope, to thereby observe the inside of the subject's body, the field of view of the observation window can be secured for satisfactory observation.

As described above, according to the present invention, the jetting port of the constant-pressure supplied gas is separated from the leading end surface on which the observation window is formed, and the jetting region of the constant-pressure supplied gas is separated by the region separating member from the region of view of the observation window. Accordingly, even if bubbles are generated by the constant-pressure supplied gas jetted near the jetting port of the constant-pressure supplied gas, the bubbles are prevented from moving toward the region of view of the observation window, so that the field of view of the observation window can be secured.

BRIEF DESCRIPTION OF THE DRAWINGS

FIG. 3A is the view observed at a position higher than that of FIG. 3B;

DETAILED DESCRIPTION OF THE PREFERRED EMBODIMENTS

Hereinafter, an attachment for an endoscope and an endoscope system according to the present invention are described in detail with reference to the attached drawings.

Figure 1:
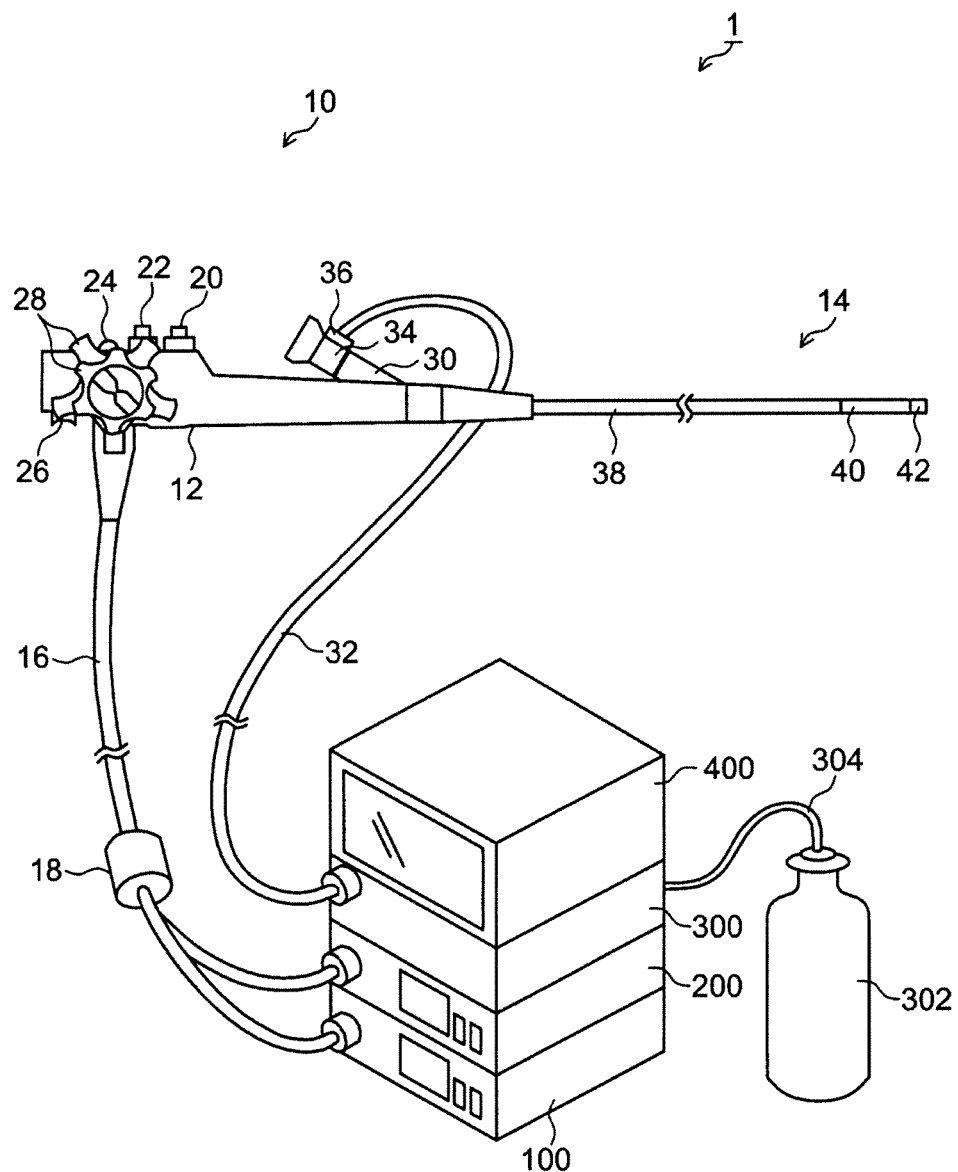
FIG. 1 is an external view schematically illustrating an overall configuration of an embodiment of an endoscope system according to the present invention.

FIG. 1 is an external view schematically illustrating an overall configuration of an embodiment of an endoscope system according to the present invention.

As illustrated in FIG. 1, an endoscope system 1 mainly includes an endoscope (flexible endoscope) 10, a light source apparatus 100, an endoscope processor 200, a gas supply apparatus 300, and a monitor apparatus 400. These apparatuses do not necessarily need to be configured as separate members as illustrated in FIG. 1. For example, the light source apparatus 100 may be built in the endoscope processor 200.

The endoscope 10 includes a hand-side operation part 12 and an insertion part 14 provided continuously with the hand-side operation part 12. An operator grips the hand-side operation part 12 to operate the endoscope 10, and inserts the insertion part 14 into a lumen of a stomach, a large intestine, or other organs of a subject, to thereby perform observation and diagnosis or curative treatment.

A universal cable 16 is connected to the hand-side operation part 12, and an LG connector 18 is provided to the leading end of the universal cable 16. The LG connector 18 is detachably coupled to the light source apparatus 100, whereby illumination light is supplied to an illumination optical system (not illustrated) provided in a leading end part of the insertion part 14. In addition, an electrical connector is connected to the LG connector 18 via the universal cable 16, and the electrical connector is detachably coupled to the endoscope processor 200. With this configuration, data of an observation image obtained by the endoscope 10 is outputted to the endoscope processor 200, and the observation image is displayed on the monitor apparatus 400 connected to the endoscope processor 200.

In addition, the hand-side operation part 12 is provided with a gas supply/water supply button 20, a suction button 22, a shutter button 24, a seesaw switch 26 for a zoom operation, a pair of angle knobs 28, and a forceps insertion part 30.

The forceps insertion part 30 is communicated with a forceps channel (not illustrated) formed inside of the insertion part 14, and as described later, the forceps channel is communicated with a forceps port (see FIG. 2) in the endoscope leading end part. In addition, when carbon dioxide gas is supplied as a constant-pressure supplied gas into the lumen via the forceps channel, an insertion port adapter 34 is attached to the forceps insertion part 30, and a gas supply tube 32 is coupled to a gas supply ferrule 36 of the insertion port adapter 34. In addition, another end of the gas supply tube 32 is coupled to the gas supply apparatus 300.

In addition, a carbon dioxide gas cylinder 302 is coupled to the gas supply apparatus 300 via a high-pressure gas tube 304. The carbon dioxide gas is reserved in the carbon dioxide gas cylinder 302 in the form of a liquid. Then, the gas supply apparatus 300 introduces the carbon dioxide gas reserved in the carbon dioxide gas cylinder 302 into the forceps channel from the forceps insertion part 30 via the gas supply tube 32 with the pressure of the carbon dioxide gas being adjusted to a predetermined value, and then jets the carbon dioxide gas into the lumen of the subject from the forceps port in the endoscope leading end part.

In addition, the insertion part 14 includes a flexible part 38, a bending part 40, and a leading end part 42. The bending part 40 is remotely operated for bending by turning the pair of angle knobs 28 provided in the hand-side operation part 12. This enables the leading end part 42 to face a desired direction.

Figure 2:
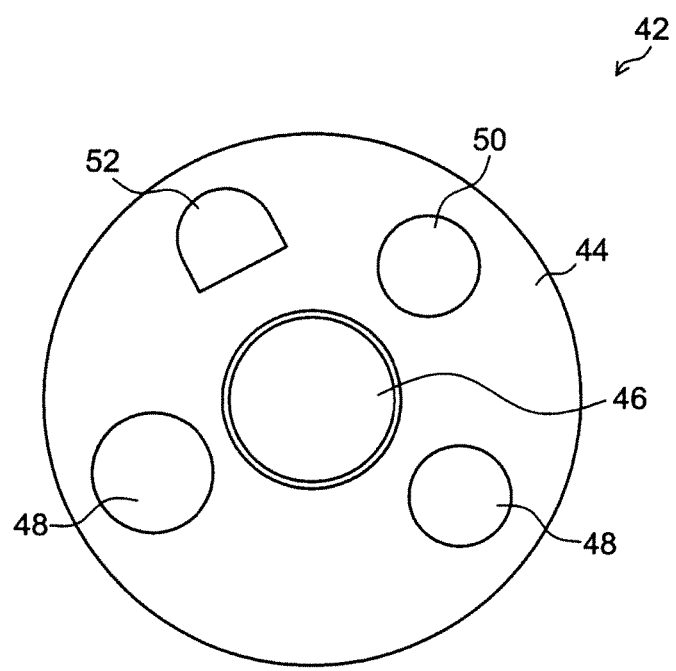
FIG. 2 is a plan view illustrating a leading end surface of a leading end part of an insertion part.

FIG. 2 illustrates a leading end surface of the leading end part 42 of the insertion part 14.

As illustrated in FIG. 2, an observation window 46, illumination windows 48, a forceps port 50, and a gas supply/water supply nozzle 52 are provided on a leading end surface 44 of the leading end part 42.

An optical system (observation optical system) for taking in image light inside of the subject's body is provided on the inner side of the observation window 46, and the taken-in image light representing an observation image is received by the CCD and is sent to the endoscope processor 200 via a signal cable. Then, the image light is converted into a video signal by the endoscope processor 200, and the observation image is displayed on the monitor apparatus 400 connected to the endoscope processor 200.

As illustrated in FIG. 2, the two illumination windows 48 are placed symmetrically with respect to the observation window 46, and an observation region inside of the subject's body is illuminated with the illumination light from the light source apparatus 100. The light from the light source apparatus 100 is guided to the illumination window 48 by an optical fiber (light guide) provided in the insertion part 14. Then, the illumination light is emitted through an illumination lens provided at the leading end and a cover glass fitted into the illumination window 48.

The forceps port 50 is connected to the forceps channel (not illustrated) provided inside of the insertion part 14, and is communicated with the forceps insertion part 30 of the operation part 12. The leading ends of forceps or other various treatment tools inserted through the forceps insertion part 30 are exposed at the forceps port 50 via the forceps channel.

In addition, particularly in the present embodiment, the carbon dioxide gas is supplied as the constant-pressure supplied gas into the lumen from the forceps port 50 via the forceps channel. When the carbon dioxide gas is supplied into the lumen, the insertion port adapter 34 is attached to the forceps insertion part 30, and the carbon dioxide gas is supplied into the lumen from the gas supply ferrule 36 of the insertion port adapter 34 via the gas supply tube 32 coupled to the gas supply apparatus 300.

The gas supply/water supply nozzle 52 serves to spray a cleaning solution and pressurized air when the observation window 46 becomes dirty, to thereby clean the observation window 46. The gas supply/water supply nozzle 52 jets fluids such as air and cleaning water toward the observation window 46 in response to a gas supply operation and a water supply operation on the gas supply/water supply button 20 provided in the operation part 12. As a result, a bodily fluid and dirt attached to the observation window 46 are wiped, to thereby secure an excellent field of view.

Unfortunately, in the case where the carbon dioxide gas is supplied into the lumen from the forceps port 50, bubbles are generated by a bodily fluid or water attached to the leading end surface 44, and the generated bubbles may cover the observation window 46, to thereby block the field of view of the observation window 46. Consequently, the observation window 46 needs to be frequently cleaned using the gas supply/water supply nozzle 52.

In view of this, in the present embodiment, even if bubbles are generated by the carbon dioxide gas jetted from the forceps port 50 and a liquid attached to the leading end surface 44, a technical idea is adopted for preventing the bubbles from moving toward a region of view of the observation window 46. Hereinafter, the technical idea is described.

Figure 3A:
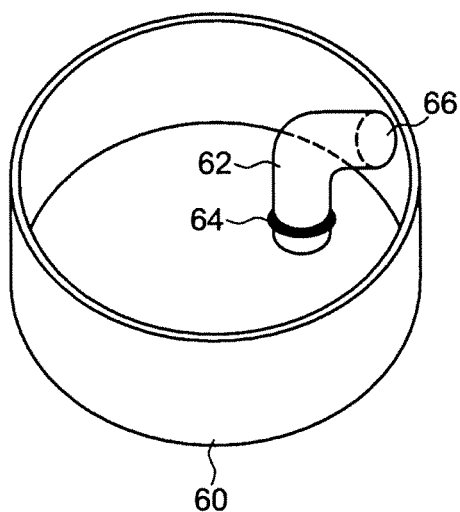
FIGS. 3A and 3B are perspective views each illustrating a hood attached to an endoscope leading end part.
Figure 3B:
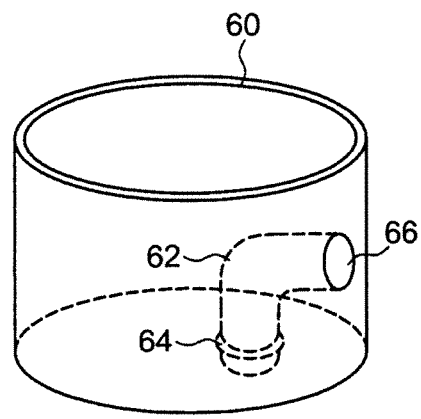

FIGS. 3A and 3B each illustrate a hood attached to the endoscope leading end part. The hood has a function of preventing bubbles generated on the leading end surface 44 from moving toward the region of view of the observation window 46.

FIG. 3A is a perspective view illustrating a state where the hood is looked down at a considerably high position, and FIG. 3B is a perspective view illustrating a state where the hood is looked at a position lower than that of FIG. 3A.

As illustrated in FIGS. 3A and 3B, a hood 60 has a cylindrical shape with a given thickness, and a thin pipe (pipe conduit) 62 bent in an L-shape is provided inside of the hood 60. The pipe 62 is formed of: a portion (horizontal part) substantially perpendicular to a side surface of the hood 60; and a portion (vertical part) that is bent by about 90° from the horizontal part and is parallel to the axial direction of the hood 60. That is, when the hood 60 is attached to the endoscope leading end part, the horizontal part of the pipe 62 is perpendicular to the axial line direction of the endoscope, and the vertical part of the pipe 62 is parallel to the axial line direction of the endoscope.

An end of a portion of the pipe 62 substantially perpendicular to the side surface of the hood 60 is connected to an opening 66 formed on the side surface of the hood 60. In addition, an end of a portion of the pipe 62 parallel to the axial direction of the hood 60 extends up to substantially the same position as that of a base-side end of the hood 60, and an O-ring 64 is provided in a leading end part of this portion of the pipe 62.

Figure 4:
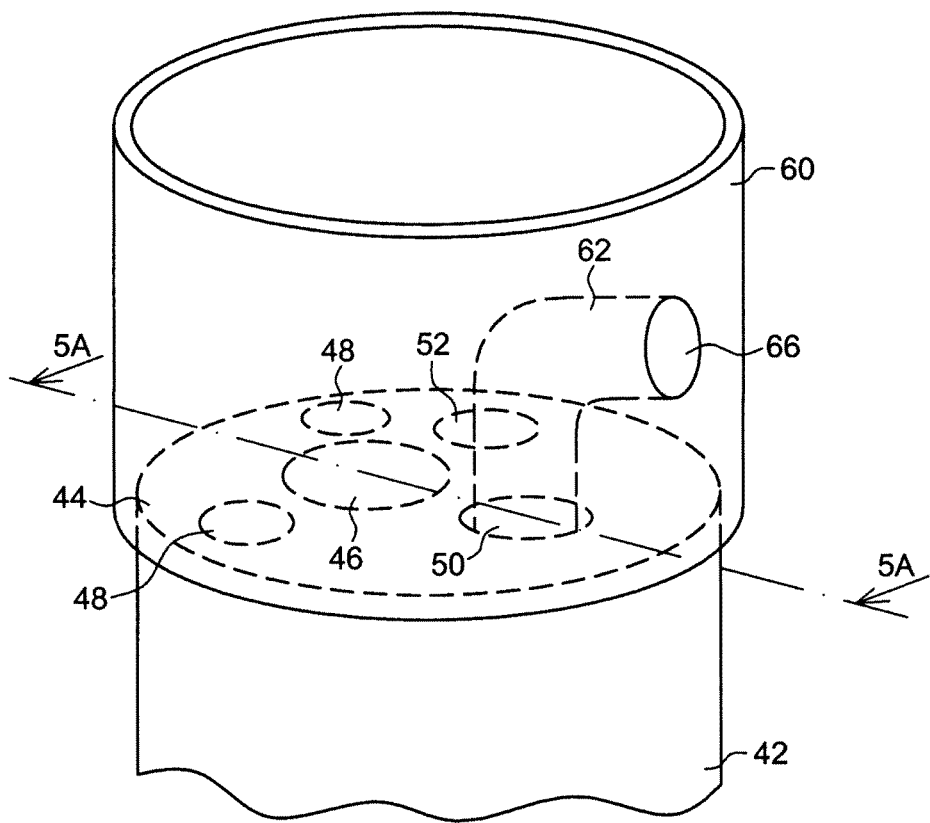
FIG. 4 is a perspective view illustrating a state where the hood is attached to the endoscope leading end part.

FIG. 4 is a perspective view illustrating a state where the hood 60 is attached to the leading end part 42 of the endoscope 10.

As illustrated in FIG. 4, the hood 60 is attached in such a manner that the leading end part 42 is fitted into an inner circumferential surface of the hood 60. Note that, an attachment part (not illustrated) for fitting the hood 60 onto an outer circumferential surface of the leading end part 42 is formed on the base end side (the side attached to the leading end part 42) of the hood 60. In this regard, an attachment part corresponding to the attachment part of the hood 60 may also be formed in the leading end part 42. The structures of these attachment parts are not particularly limited. In addition, the materials of the hood 60 and the pipe 62 are not particularly limited, and for example, a resin material may be used.

Then, when the hood 60 is attached to the leading end part 42, an end of the portion (vertical part) of the L-shaped pipe 62, which is parallel to the axial direction of the hood 60, is exactly fitted into an inner circumferential surface of the forceps port 50 formed on the leading end surface 44 of the leading end part 42.

Figure 5:
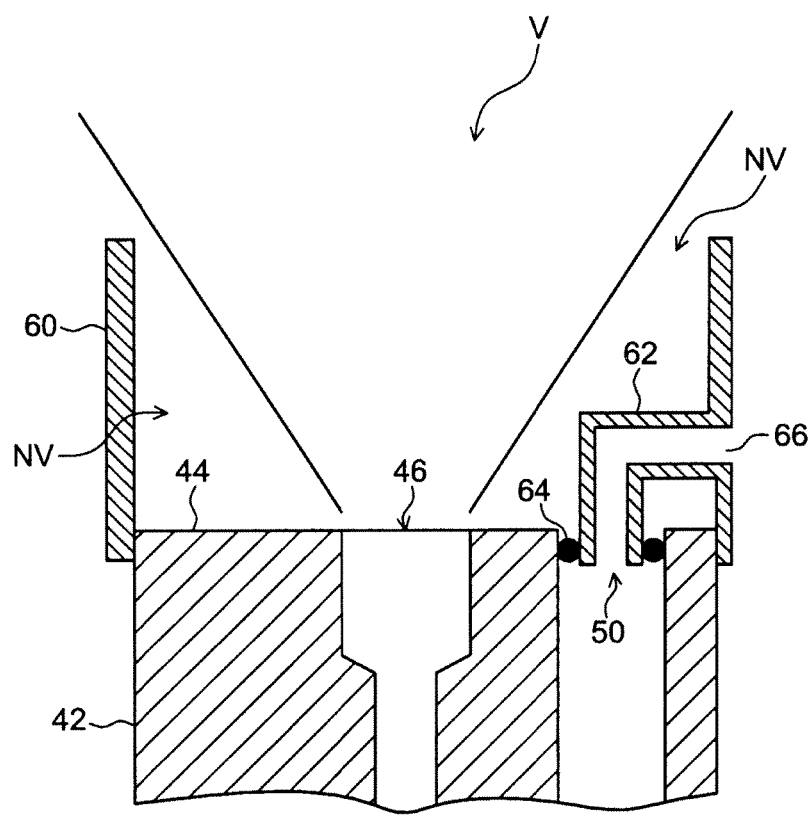
FIG. 5 is a cross-sectional view taken along a plane including the line 5A-5A in FIG. 4 and being parallel to the axial direction of the hood.

Next, FIG. 5 is a cross-sectional view illustrating the hood 60 and the leading end part 42 in FIG. 4 that are taken along a plane including the dashed-dotted line 5A-5A drawn on the leading end surface 44 in FIG. 4 and being parallel to the axial direction of the hood 60.

As illustrated in FIG. 5, when the hood 60 is fitted for attachment onto the leading end part 42 of the endoscope 10, one end (on the vertical part side) of the L-shaped pipe 62 is fitted into the forceps port 50. At this time, because the O-ring 64 is provided near the one end of the pipe 62, the pipe 62 can be fitted into the forceps port 50 with high airtightness. This can prevent the carbon dioxide gas from leaking from the forceps port 50. In addition, another end (on the horizontal part side) of the pipe 62 having the one end (on the vertical part side) fitted into the forceps port 50 is coupled to the opening 66 formed on the side surface of the hood 60.

In this way, the forceps port 50 is communicated with the opening 66 formed on the side surface of the hood 60 via the L-shaped pipe 62, whereby the carbon dioxide gas is jetted from the opening 66 formed on the side surface of the hood 60 when the carbon dioxide gas is supplied into the lumen through the forceps port 50.

On the other hand, because the circumference of the observation window 46 is surrounded by the hood 60, even if bubbles are generated by the carbon dioxide gas jetted from the opening 66 formed on the side surface of the hood 60, the bubbles do not block the field of view of the observation window 46.

Note that, as illustrated in FIG. 5, the entire body of the pipe 62 is provided in a region outside of view NV that is outside of a region of view V of the observation window 46, and hence the pipe 62 itself does not block the field of view of the observation window 46.

Figure 6:
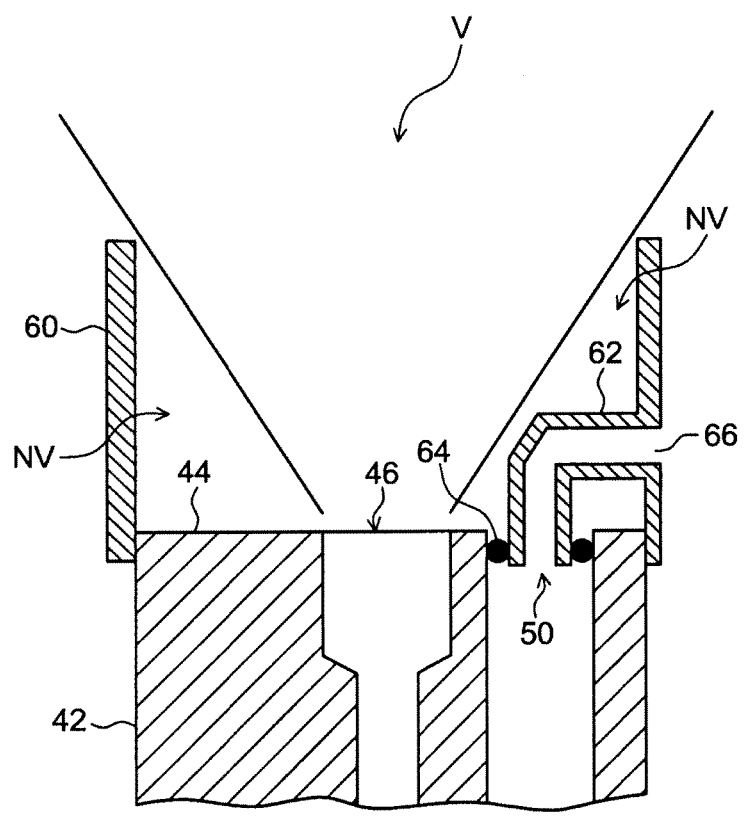
FIG. 6 is a cross-sectional view illustrating a modified example of the hood illustrated in FIG. 5.

In addition, part of the pipe 62 may overlap with the region of view V depending on the positional relation between the observation window 46 and the forceps port 50 on the leading end surface 44, the sizes thereof, and other factors. In such a case, for example, a corner portion of the pipe 62 may be obliquely cut out as illustrated in FIG. 6 such that the entire body of the pipe 62 falls within the region outside of view NV. This can prevent the pipe 62 itself from blocking the field of view of the observation window 46.

As described above, according to the present embodiment, the hood 60 is attached to the leading end part 42, the forceps port 50 is communicated with the opening 66 formed on the side surface of the hood 60 by the L-shaped pipe 62 formed inside of the hood 60, and the carbon dioxide gas supplied via the forceps channel is jetted from the opening 66 formed on the side surface of the hood 60. With this configuration, even if bubbles are generated by the carbon dioxide gas jetted from the opening 66, the bubbles do not move toward the observation window 46, and thus do not block the field of view of the observation window 46. Accordingly, the field of view of the observation window 46 can be sufficiently secured.

In addition, in the embodiment described above, the carbon dioxide gas is supplied into the lumen from the forceps port via the forceps channel, but the present invention is not limitedly applied to the case where the carbon dioxide gas is supplied from the forceps port.

For example, the present invention can also be applied to the case where a pipe conduit for constant-pressure gas supply that is dedicated to gas supply is provided in the insertion part separately from the forceps channel, an opening of the pipe conduit is provided on the leading end surface, the carbon dioxide gas is supplied via the pipe conduit for constant-pressure gas supply, and the carbon dioxide gas is jetted into the lumen from the opening thereof formed on the leading end surface.

At this time, when the hood 60 is attached to the leading end part 42, the one end (on the vertical part side) of the L-shaped pipe 62 provided inside of the hood 60 is fitted into the opening of the pipe conduit for constant-pressure gas supply, the opening being formed on the leading end surface 44. Then, the opening of the pipe conduit for constant-pressure gas supply and the opening 66 formed on the side surface of the hood 60 are communicated with each other by the pipe 62.

With this configuration, the carbon dioxide gas supplied via the pipe conduit for constant-pressure gas supply is jetted from the opening 66 formed on the side surface of the hood 60, and hence generated bubbles do not block the field of view of the observation window 46.

As described above, in the present invention, the L-shaped pipe (pipe conduit) 62 is coupled to the opening formed on the leading end surface 44 from which the constant-pressure supplied gas (carbon dioxide gas) is jetted, the another end of the pipe 62 is coupled to the opening 66 formed on the side surface of the hood 60, and the gas is jetted from the opening 66. Further, the region of view of the observation window 46 formed on the leading end surface 44 is separated (sectioned) by the hood 60 from a jetting region in which the gas is jetted from the opening 66. In this manner, bubbles are prevented from blocking the field of view of the observation window 46, so that the field of view is secured.

In addition, a member for preventing bubbles from blocking the field of view of the observation window 46 in this way is not limited to the hood 60 that surrounds the entire circumference of the leading end part 42.

Figure 7:
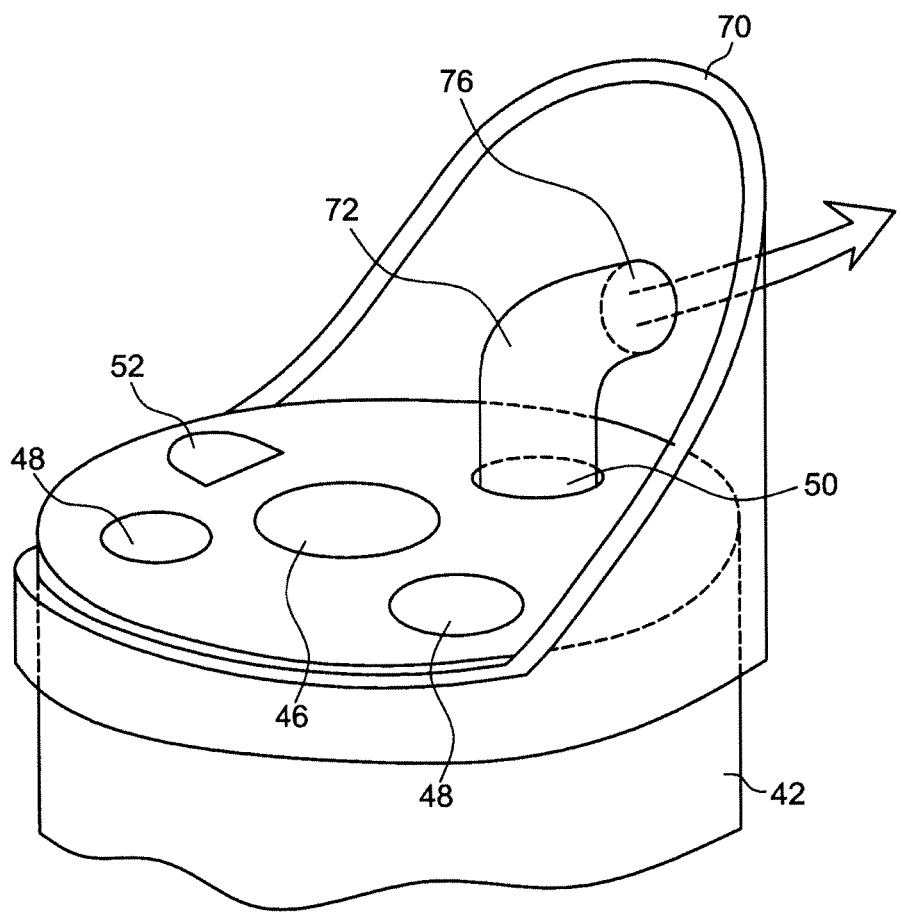
FIG. 7 is a perspective view illustrating a state where an attachment other than the hood is attached to the endoscope leading end part.

For example, as illustrated in FIG. 7, such a member as an attachment 70 may be adopted instead of the hood 60, and the attachment 70 is formed in a wall-like manner on part of an outer circumferential surface of the leading end surface 44 so as to follow the outer circumferential surface on the side on which the forceps port 50 is formed. As illustrated in FIG. 7, the attachment 70 formed in a wall-like manner has a shape obtained by obliquely cutting out part of a leading end part of a cylinder.

In addition, similarly to the hood 60, an L-shaped pipe 72 is provided to the attachment 70, and the L-shaped pipe 72 is formed of: a horizontal part perpendicular to the axial direction of the endoscope; and a vertical part parallel to the axial direction of the endoscope. One end (on the horizontal part side) of the pipe 72 is coupled to an opening 76 formed on the side surface of the attachment 70, and another end (on the vertical part side) thereof is coupled to the forceps port 50.

Note that, similarly to the above-mentioned example, an O-ring (not illustrated) for maintaining airtightness is provided at an end of a portion (vertical part) of the pipe 72, the portion being coupled to the forceps port 50.

As indicated by an arrow in FIG. 7, the constant-pressure supplied gas (carbon dioxide gas) supplied via the forceps port 50 is jetted to the side opposite to the observation window 46 from the opening 76 formed on the side wall of the attachment 70. Accordingly, even if bubbles are generated near the opening 76, the side wall of the attachment 70 can prevent the bubbles from moving toward the region of view of the observation window 46.

Hereinabove, the attachment for the endoscope and the endoscope system according to the present invention have been described in detail. It goes without saying that the present invention is not limited to the above-mentioned embodiments, and may be variously improved or modified within a range not departing from the gist of the present invention.

What is claimed is:

1. An attachment for an endoscope, the attachment being attachable to a leading end part of the endoscope having a leading end surface on which an observation window for observing an inside of a subject's body and a first opening for jetting a constant-pressure supplied gas are formed, the attachment comprising:
    a second opening provided at a position separate from the leading end surface;
    a pipe conduit that communicates the first opening and the second opening with each other so as to jet the constant-pressure supplied gas only from the second opening; and
    a region separating member that separates a jetting region of the constant-pressure supplied gas jetted from the second opening from a region of view of the observation window,
    wherein the region separating member comprises a cylindrically shaped hood fitted onto an outer circumferential surface of the leading end part, an entirety of the hood being provided in a region outside of view that is outside of a region of view of the observation window,
    wherein the second opening is formed on a side surface of the hood on a side close to the first opening,
    wherein the pipe conduit comprises a pipe-like member that is bent in an L-shape and includes:
    a horizontal part perpendicular to an axial direction of the endoscope; and
    a vertical part parallel to the axial direction of the endoscope, with the pipe-like member being attached to the leading end part of the endoscope, and
    wherein the pipe conduit is provided to the hood so that an opening of the horizontal part is coupled to the second opening and an opening of the vertical part can be coupled to the first opening.

2. The attachment for an endoscope according to claim 1, further comprising an O-ring that is provided in a leading end part of the vertical part of the pipe conduit, the leading end part being coupled to the first opening.

3. The attachment for an endoscope according to claim 1, wherein the region separating member comprises a wall-like member that is formed so as to follow an outer circumferential surface of the leading end surface on a side on which the first opening is formed.

4. The attachment for an endoscope according to claim 3, wherein the wall-like member has a shape obtained by obliquely cutting out a leading end of a cylinder.

5. An endoscope system comprising the attachment for an endoscope according to claim 3.

6. The attachment for an endoscope according to claim 4, wherein the second opening is formed in the wall-like member.

7. The attachment for an endoscope according to claim 4, wherein an entire body of the pipe conduit is provided in a region outside of view that is outside of the region of view of the observation window.

8. An endoscope system comprising the attachment for an endoscope according to claim 4.

9. The attachment for an endoscope according to claim 1, wherein an entire body of the pipe conduit is provided in a region outside of view that is outside of the region of view of the observation window.

10. The attachment for an endoscope according to claim 1, wherein a corner portion of the pipe-like member has an oblique surface such that an entire body of the pipe conduit is provided in a region outside of view that is outside of the region of view of the observation window.

11. An endoscope system comprising:
    an endoscope having a leading end surface on which an observation window for observing an inside of a subject's body and a first opening for jetting a constant-pressure supplied gas are formed; and
    an attachment for the endoscope being attached to a leading end part of the endoscope,
    the attachment comprising:
    a second opening provided at a position separate from the leading end surface;
    a pipe conduit that communicates the first opening and the second opening with each other so as to jet the constant-pressure supplied gas only from the second opening; and
    a region separating member that separates a jetting region of the constant-pressure supplied gas jetted from the second opening from a region of view of the observation window,
    wherein the region separating member comprises a cylindrically shaped hood fitted onto an outer circumferential surface of the leading end part, an entirety of the hood being provided in a region outside of view that is outside of a region of view of the observation window,
    wherein the second opening is formed on a side surface of the hood on a side close to the first opening,
    wherein the pipe conduit comprises a pipe-like member that is bent in an L-shape includes:
    a horizontal part perpendicular to an axial direction of the endoscope; and
    a vertical part parallel to the axial direction of the endoscope, with the pipe-like member being attached to the leading end part of the endoscope, and
    wherein the pipe conduit is provided to the hood so that an opening of the horizontal part is coupled to the second opening and an opening of the vertical part can be coupled to the first opening.

* * * * *